US00PP34918P2

(12) United States Plant Patent
White

(10) Patent No.: US PP34,918 P2
(45) Date of Patent: Jan. 17, 2023

(54) ***DAPHNE* PLANT NAMED 'BLACIR'**

(50) Latin Name: ***Daphne* hybrid**
Varietal Denomination: Blacir

(71) Applicant: Anthony Robin White, Kilmeston (GB)

(72) Inventor: Anthony Robin White, Kilmeston (GB)

(73) Assignee: SUSAN BARBARA WHITE, Alresford (GB)

( * ) Notice: Subject to any disclaimer, the term of this patent is extended or adjusted under 35 U.S.C. 154(b) by 0 days.

(21) Appl. No.: 17/699,648

(22) Filed: Mar. 21, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP18,361 P2 * 12/2007 White ..... A01H 6/00
Plt./226

* cited by examiner

*Primary Examiner* — Karen M Redden
(74) *Attorney, Agent, or Firm* — Penny J. Aguirre

(57) ABSTRACT

A new cultivar of *Daphne* named 'Blacir' that is characterized by its bushy growth habit with natural branching (not requiring pinching), its height of 45 to 60 cm, its bright green and glossy foliage, its fragrant flowers that are deep pink in color, and its long blooming habit.

2 Drawing Sheets

Botanical classification: *Daphne* hybrid.
Variety denomination: 'Blacir'.

CROSS-REFERENCE TO A RELATED APPLICATION

This application claims priority to European Community Plant Variety Office (CPVO) Plant Breeder's Rights Application No. 2022/0503 filed on Feb. 21, 2022, under 35 U.S.C. 119(f), the entire contents of which is incorporated by reference herein.

BACKGROUND OF THE INVENTION

The present invention relates to a new and distinct cultivar of *Daphne* of hybrid origin. The new cultivar will be referred to hereafter by its cultivar name, 'Blacir'. 'Blacir' is a new cultivar of *Daphne* grown for use as a landscape shrub.

The new cultivar arose as a controlled breeding program by the Inventor in Kilmeston, Alresford, United Kingdom. The objective of the breeding program was to develop a new cultivar of *Daphne* with flowers that are bright in color, fragrant, and long blooming combined with tolerance to a wide range of growing conditions with ease of propagation. The Inventor made a cross between an unnamed plant of *Daphne circassica* as the female parent and an unnamed plant of *Daphne sericea* as the male parent in June of 2011. The Inventor selected the new cultivar as a single unique plant from the above cross in 2016.

Asexual propagation of the new cultivar was first accomplished by stem cuttings by the Inventor in 2014 in Kilmeston, Alresford, United Kingdom and further evaluated. Asexual propagation by stem cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blacir' as a new and unique cultivar of *Daphne*.

1. 'Blacir' exhibits a bushy growth habit with natural branching (not requiring pinching).
2. 'Blacir' exhibits a height of 45 to 60 cm.
3. 'Blacir' exhibits bright green, glossy foliage.
4. 'Blacir' exhibits fragrant flowers that are deep pink in color.
5. 'Blacir' exhibits a long blooming habit.

The female parent of 'Blacir' differs from 'Blacir' in having a tighter and lower growing growth habit. The male parent of 'Blacir' differs from 'Blacir' in having a more open plant habit and a taller plant height. 'Blacir' can be most closely compared to typical plants of *Daphne tangutica* and *Daphne* x *transatlantica* 'Blapink' (not patented). Typical plants of *Daphne tangutica* differ from 'Blacir' in having a more open plant habit, leaves that are longer with a glabrous margin, and flowers with sepal tubes that are rosy purple in color, sepal lobes that are white in color and top stamens that are inserted. 'Blapink' differs from 'Blacir' in having flowers that are lighter pink in color in summer.

BRIEF DESCRIPTION OF THE DRAWINGS

The accompanying colored photographs illustrate the overall appearance and distinct characteristics of the new

*Daphne*. The photographs were taken of a 6-year-old plant of the new cultivar as grown outdoors in a 27-cm container in Boskoop, the Netherlands.

Figure 1:
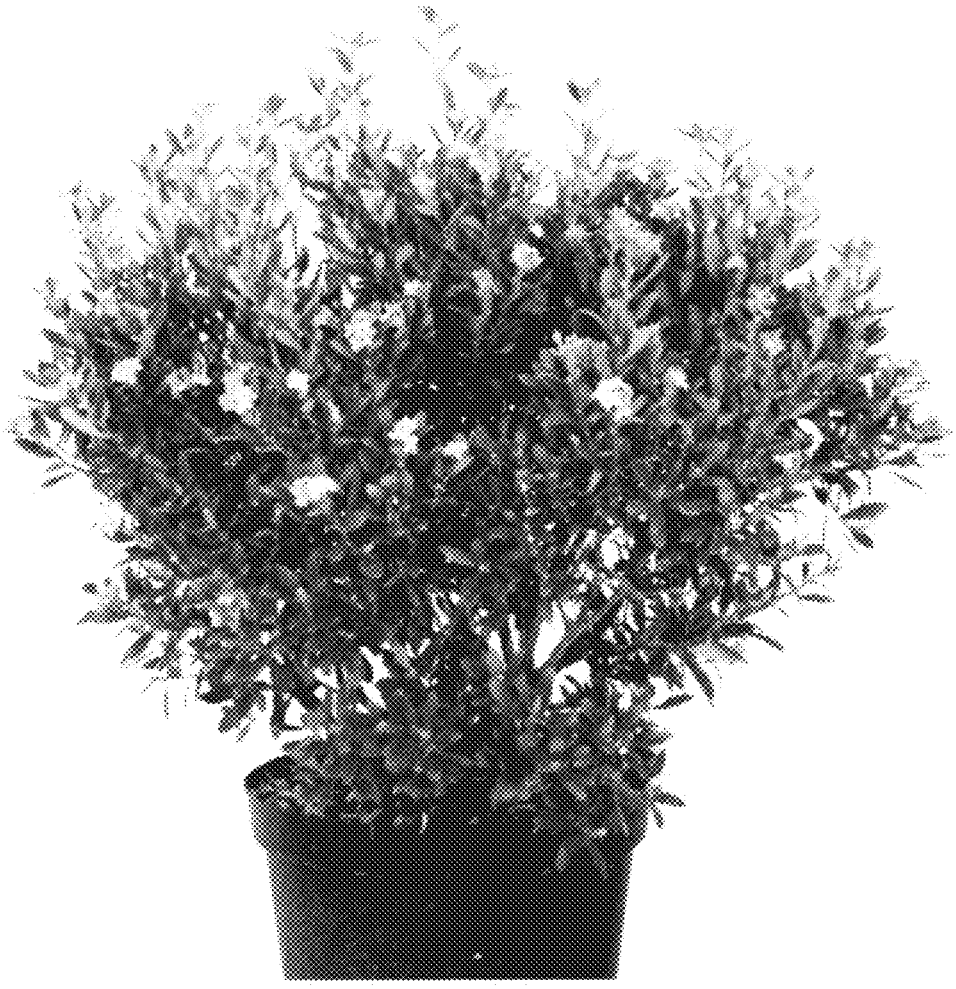

The photograph in FIG. 1 provides a side view of 'Blacir' in bloom.

Figure 2:
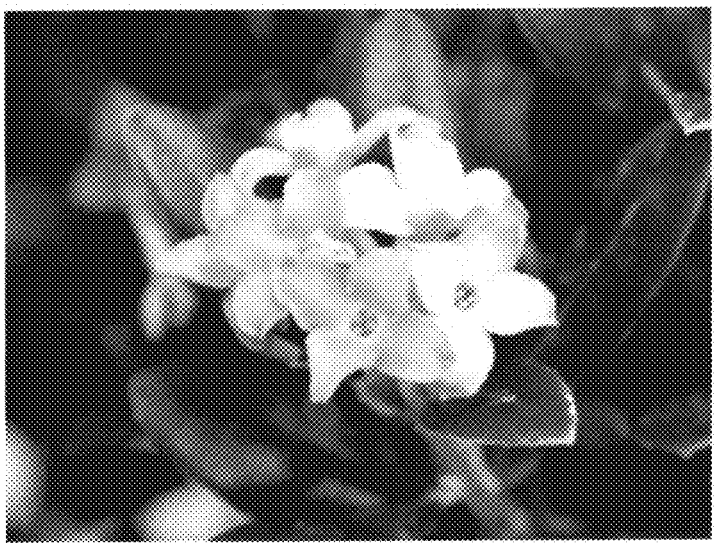

The photograph in FIG. 2 provides a close-up view of an inflorescence of 'Blacir'.

Figure 3:
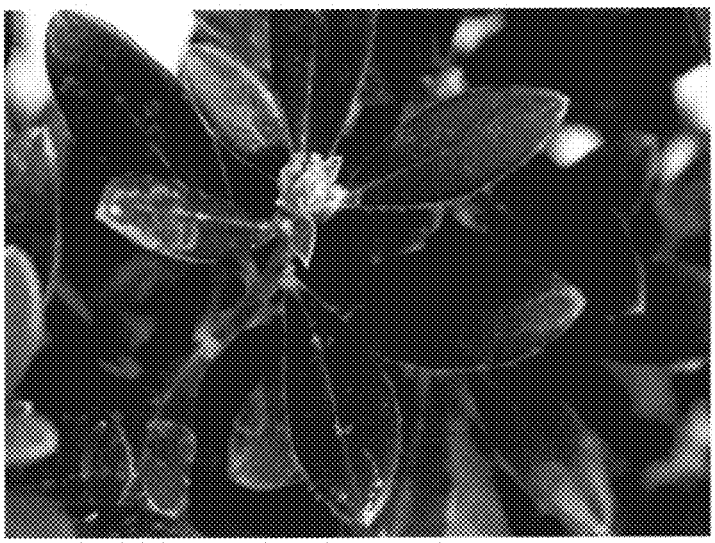

The photograph in FIG. 3 provides a close-up view of the foliage of 'Blacir'.

The colors in the photographs are as close as possible with the photographic and printing technology utilized and the color values cited in the detailed botanical description accurately describe the colors of the new *Daphne*.

DETAILED BOTANICAL DESCRIPTION

The following is a detailed description of 6-year-old plants of the new cultivar as grown outdoors in 27-cm circular containers in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit*.—February to May and July to November provide the most abundant blooms with very sparse flowering in May to July in the United Kingdom, blooming is depending on weather conditions.

*Plant type*.—Evergreen shrub.

*Plant habit*.—Main flowering stems grow from the base with lateral branches.

*Height and spread*.—45 to 60 cm in height and 30 cm in spread as grown in the landscape.

*Cold hardiness*.—At least in U.S.D.A. Zones 8 but hardiness has not been tested in colder zones.

*Diseases and pests*.—No susceptibility to resistance to diseases or pests has been observed.

*Propagation*.—Stem cuttings and tissue culture.

*Growth rate*.—Moderate.

*Root description*.—Fibrous roots.

*Root development*.—6 to 8 weeks to initiate roots and a finished 9 cm container is produce in about one year.

Branch description:

*Stem shape*.—Rounded.

*Stem color*.—Young; 145B, mature; N199C, old stems; between 199B to 199D and 200C.

*Stem surface*.—Matte, stems densely covered with short soft pubescence, average length of hairs 1 mm in length and 161C in color.

*Branching*.—41 main branches emerging from base, 475 lateral branches per plant.

*Stem aspect*.—Average of 40°.

*Branch strength*.—Strong.

*Internode length*.—Average 8 mm.

*Stem size*.—Lateral branches; an average of 10.5 cm in length (excluding inflorescence) and 2 mm in diameter.

*Stipules*.—None.

Foliage description:

*Leaf type*.—Simple.

*Leaf shape*.—Obovate to ovate.

*Leaf aspect*.—Flat to slightly revolute.

*Leaf apex*.—Broad acute to obtuse.

*Leaf base*.—Cuneate.

*Leaf size*.—Average of 2.2 cm in length and 1.1 cm in width.

*Leaf arrangement*.—Alternate.

*Leaf margin*.—Entire, slightly revolute, hirsute with hairs an average of 1 mm in length and 157D in color.

*Leaf venation*.—Pinnate, mature leaf color upper surface NN137A, mature leaf color lower surface 146D.

*Leaf color*.—Young upper surface; 144A, young lower surface; 144B, mature upper surface; NN137A, mature lower surface; 191A.

*Leaf number*.—Average of 14 per lateral branch.

*Leaf surface*.—Upper surface smooth, glabrous and glossy, lower surface matte and covered with dense soft pubescent thin adpressed hairs, average length of hairs 1 mm, color is 157D.

*Petioles*.—An average of 2.5 mm in length and 1.5 mm in diameter, upper surface moderately glossy, smooth and glabrous, lower surface matte with densely covered with soft pubescent thin hairs; average 1 mm in length, color 157D, strong, color upper surface 144B, lower surface 146D.

Inflorescence description:

*Inflorescence type*.—Axillary and terminal clusters.

*Lastingness of inflorescence*.—Self-cleaning, lastingness average of 10 days.

*Inflorescence size*.—An average of 1.9 cm in height and 2.7 cm in diameter.

*Flower fragrance*.—Strong, sweet and pleasant.

*Flower number*.—Average of 8 per inflorescence, 3000 per plant.

*Flower aspect*.—Upright to outward.

*Flower bud*.—An average of 1.5 cm in length and 3 mm in width, narrow spathulate to oblanceolate in shape, matte surface, densely covered with soft pubescent thin hairs, average length of hairs: 1 mm, colored NN155D, bud color 76A, immature tube 68C.

*Flower form*.—Tubular, single.

*Flower size*.—An average of 1.6 cm in length and 1.4 cm in width, throat an average of 2 mm in diameter.

*Petals*.—None, apetalous.

*Sepals*.—An average of 4 per flower, spathulate with lobes ovate in shape, average of 1.7 cm in length, 5 mm in width, apex is emarginated and curled backwards, entire margins with fine undulation, lower 60% base fused, color; upper surface when opening N74C, lower surface when opening N75A, upper surface when fully open N75D, lower surface when fully open 77D, venation when fully open upper surface N75D, venation when fully open lower surface 77D, throat color N75D, upper surface smooth, glabrous, moderately velvety, lower surface is densely covered with soft pubescent thin hairs an average of 1 mm in length and NN155D in color.

*Sepal tube*.—An average of 1 cm in length and 2.5 mm in width, color; outer surface color 186D changing towards base to 145C, inner surface N75D, surface; outer surface densely soft pubescent with thin hairs, average length of hairs 1 mm, colored white NN155D, inner surface smooth and glabrous.

*Bracts*.—8 spirally arranged around the base, average of 6 mm in length and 2 cm in width, cuneate base, acute apex, obovate in shape, color upper surface 144A, color lower surface 144B, upper surface texture; moderately glossy, lower surface matte densely soft pubescent with thin hairs an average of 1 cm in length and color NN155D.

*Peduncles*.—None, flowers sessile to stem.

*Pedicels*.—None, flowers sessile to stem.

Reproductive organs:

*Gynoecium*.—Pistil; 1, 0.75 mm in length, stigma; club-shaped, sessile, 0.75 mm in length and width, 157C in color, style; not present, stigma sessile, ovary; 197C in color, changing towards base 150C.

*Androecium*.—Stamens; average of 8, exerted, filaments; average of 5 mm in length, implanted inside the tube with top exerted, color 157D, anthers; an average of 1 cm in length and 5 mm in width, basifixed and narrow oblanceolate in shape, 24A in color, pollen is low in quantity and 22B in color.

*Fruit and seed*.—No fruit or seed observed to date.

It is claimed:

1. A new and distinct cultivar of *Daphne* plant named 'Blacir' as herein illustrated and described.

* * * * *